United States Patent [19]

Franz

[11] Patent Number: 4,471,131

[45] Date of Patent: Sep. 11, 1984

[54] NOVEL SILYL ESTERS OF N-PHOSPHONOMETHYLGLYCINE

[75] Inventor: John E. Franz, Crestwood, Mo.

[73] Assignee: Monsanto Company, St. Louis, Mo.

[21] Appl. No.: 536,097

[22] Filed: Sep. 27, 1983

[51] Int. Cl.$^3$ .................... C07F 7/08; C07F 7/10; C07F 7/18

[52] U.S. Cl. .................................... 556/405; 71/86

[58] Field of Search ............................ 556/405; 71/86

[56] References Cited

U.S. PATENT DOCUMENTS

| | | | |
|---|---|---|---|
| 2,843,615 | 7/1958 | Linville | 556/405 |
| 3,197,431 | 7/1965 | Lanham et al. | 556/405 X |
| 3,203,925 | 8/1965 | Fekete | 556/405 X |
| 3,492,193 | 1/1970 | Tesoro | 556/405 X |
| 3,716,569 | 2/1973 | Redmore et al. | 556/405 |
| 3,799,758 | 3/1974 | Franz | 71/86 |
| 4,120,689 | 10/1978 | Dutra | 71/86 |
| 4,206,156 | 6/1980 | Kamiya et al. | 556/405 X |
| 4,367,154 | 1/1983 | Jernigan | 556/405 X |

FOREIGN PATENT DOCUMENTS 56620  5/1978  Japan ................................. 556/405

*Primary Examiner*—Paul F. Shaver
*Attorney, Agent, or Firm*—Raymond C. Loyer; Richard H. Shear; Arnold H. Cole

[57] ABSTRACT

This disclosure relates to novel silyl esters of N-phosphonomethylglycine useful as post-emergence herbicides.

67 Claims, No Drawings

NOVEL SILYL ESTERS OF N-PHOSPHONOMETHYLGLYCINE

BACKGROUND OF THE INVENTION

This invention relates to novel silyl esters of N-phosphonomethylglycine as well as to their use as post-emergence herbicides, herbicidal compositions, and herbicidal methods.

N-phosphonomethylglycine has been discovered to be a particularly useful herbicide and the herbicidal method employing such compound is disclosed in U.S. Pat. No. 3,799,758. It is taught therein that N-phosphonomethylglycine, its salts, amides, esters, and other derivatives are highly desirable herbicides. Included within the esters of U.S. Pat. No. 3,799,758 are hydrocarbon and hydrocarbonoxy hydrocarbon esters having from 1 to 18 carbon atoms in the ester group and the halogenated hydrocarbon and hydrocarbonoxyhydrocarbon groups. However, the patent discloses only the diesters of N-phosphonomethylglycine.

The benzyl and aryl triesters of N-phosphonomethylglycine are disclosed in U.S. Pat. No. 4,120,689. The triesters and the hydrolysis products thereof containing at least one benzyloxy or aryloxy group are useful as post-emergence herbicides.

Japanese Patent Publication LOP No. 56520/1978 (published May 23, 1978) describes as an intermediate a trimethylsilyl ester of N-phosphonomethylglycinonitrile. This intermediate is easily hydrolyzed at room temperature by addition of a water/methanol mixture to give:

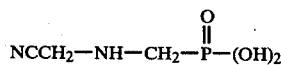

DESCRIPTION OF THE INVENTION

The novel silyl esters of this invention are represented by the structure

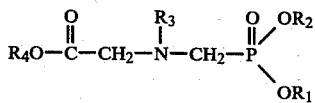

wherein $R_1$ and $R_2$ are independently selected from hydrogen, aryl, benzyl, substituted aryl and substituted benzyl groups, and X wherein X is

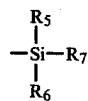

wherein $R_5$ and $R_6$ are independently selected from alkyl groups having from 1 to 4 carbon atoms, phenyl and phenyl substituted with from 1 to 3 substituents selected from halogen, lower alkyl lower alkoxy, —$CF_3$, nitro and cyano and $R_7$ is a tertiary alkyl group having from 4 to 7 carbon atoms, $R_3$ is hydrogen or a herbicidally non-interfering group, and $R_4$ is selected from hydrogen, X, alkyl groups having from 1 to 8 carbon atoms, lower alkoxyalkyl, phenoxyalkyl, napthyl, benzyl, phenyl and phenyl substituted with from 1 to 3 substituents selected from halogen, lower alkyl lower alkoxy, nitro, trifluoromethyl and cyano provided that at least one of $R_1$, $R_2$, and $R_4$ is X.

The term "halogen" as employed herein means chlorine, bromine, and iodine.

The term "lower alkyl" means straight and branched chained alkyl radicals having from 1 to 4 carbon atoms.

The term "lower alkoxy" means straight and branched chain alkoxy radicals having from 1 to 4 carbon atoms.

The term "aryl" means phenyl and naphthyl. The aryl and benzyl groups can be substituted with from 1 to 3 substituents selected from halogen, alkyl, alkoxy, lower alkyl lower alkoxy, nitro, trifluoromethyl and cyano. However, it is preferred that these groups have only one or two substituents.

The term "herbicidally non-interfering group" means those groups of atoms which permit retention of substantial herbicidal activity. There is known in the prior art numerous herbicidally active derivatives of N-phosphonomethylglycine having herbicidally non-interfering N-substitution. However, other known compounds structurally similar to N-phosphonomethylglycine, varying only by N-substitution, have little or no herbicidal properties. Because some compounds having substituents on the nitrogen atom exhibit little or no herbicidal activity, while others exhibit significant herbicidal activity, there has developed in the prior art known N-substituent groups which are considered herbicidally non-interfering. An example of a herbicidally interfering N-substituent is the alkyl group. N-alkyl, N-phosphonomethylglycine derivatives have been observed to have practically no herbicidal properties. However, N-alkyl-N-phosphonomethylglycine-N-oxides possess considerable post-emergence herbicidal activity.

Typical herbicidally non-interfering N-substituent groups in compounds of this invention are, for example, N-organo-N-nitroso groups such as are disclosed in U.S. Pat. No. 4,062,699, N-nitroso, N-hydroxy and N-perfluoroacyl groups. Additional herbicidally non-interfering N-substituents are described in the following U.S. patents which are hereby incorporated by reference together with the above-mentioned U.S. patent. Please see U.S. Pat. Nos. 4,130,412; 4,131,448; 4,175,946; 4,195,983; 4,199,345; 4,251,256; 4,261,727; and 4,322,239.

Illustrative of substituted phenyl, benzyl, and naphthyl groups represent are for example, mono and dihalophenyl such as chlorophenyl, dichlorophenyl, chlorobromophenyl, bromophenyl, diiodophenyl, fluorophenyl, chloronaphthyl, chlorobenzyl, dichlorobenzyl, 2,3 or 4-methylbenzyl, 2,3 or 4-chlorobenzyl, 2,3 or 4-nitrobenzyl, lower alkoxy substituted derivatives such as methoxy, ethoxy, propoxy or butoxyphenyl, benzyl or naphthyl, 2,3 and 4-nitrophenyl, trifluoromethylphenyl, trifluoromethylbenzyl, 2-chloro-4-methyl phenyl, 2-methyl-4-chlorophenyl and the like.

Certain members of the substituent groups on the phenyl, benzyl, and napthyl ring may exhibit steric hindrance in processes of manufacture, as, for example, t-butyl groups. In such event tri-substitution will usually occur on nonadjacent positions of the aryl nucleus. Otherwise, the substituent groups are not limited by any particular location on the ring.

The novel silyl esters of this invention are prepared by the reaction of N-phosphonomethylglycine or its carboxylic esters with trialkyl(halo)silane in an aprotic solvent. An acid acceptor is included in the reaction mixture to accept protons thereby maintaining the reaction mixture neutral or basic. There is possible the formation of mono-, di-, and trisilyl esters of N-phosphonomethylglycine. In general, the diester is produced by the abovementioned reaction unless there is provided a stochiometric excess of trialkyl(halo)silane so as to provide the triester. The monoester is provided by hydrolysis of the diester.

The process for providing the novel silyl esters of this invention is described by the following reaction sequence:

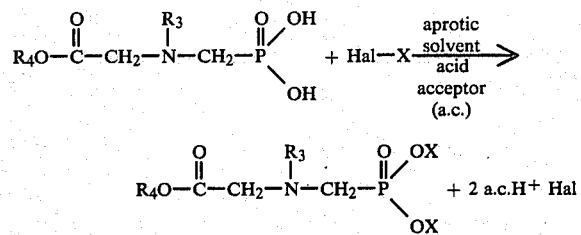

wherein $R_3$, $R_4$, and X are as defined above.

The silyl ester is typically recovered from the reaction mixture by evaporating the solvent. Purification is obtained by further dissolution, filtering, and solvent evaporation.

The monoester is easily obtained by hydrolysis of the diester using any convenient hydroxyl containing solvent such as water, methanol, or ethanol. The reaction occurs readily at ambient temperature such as from 10° C. to 40° C. and preferrably 15° C. to 20° C. In some instances hydrolysis will occur upon contact with atmospheric moisture.

When preparing the di- and triesters of this invention non-aqueous systems are employed and care is taken to prevent hydrolysis by a trace amount of water in the reagents employed. Accordingly, it is customary to employ previously dried vessels and reagents.

The above-described reaction is carred out at temperatures in the range of from 20° C. to 100° C. or higher. Usually satisfactory results are obtained at temperatures in the range of from 30° C. to 50° C. The solvent is selected so as to be conveniently retained in the reaction mixture at the operating temperature and conveniently separated from the product after completion of the reaction. The solvent can be any suitable aprotic inert solvent such as benzene, acetonitrile, dioxane, toluene, xylene, tetrahydrofuran diethyl ether, chloroform, carbon tetrachloride, dichlorobenzene, and ethylene glycol dimethyl ether.

The acid acceptor is typically an amine, preferrably a tertiary amine, which will not react with the other reactants employed as produced by the reaction. Examples of suitable tertiary amines include trimethylamine, triethyamine, tributylamine, trihexylamine, 1,5-diazabicyclo-[5.4.0]-undec-5-ene, pyridine, quinoline, mixtures thereof, and the like.

EXAMPLE 1

Preparation of Glycine, N-((bis[(((1,1-Dimethylethyl)Diphenoxysilyl)oxy]-Phosphinyl)Methyl)-, 1-Methylethyl Ester Utilizing dried glass equipment, 5 g (0.0237 mol) of 1-methylethyl-N-phosphonomethylglycinate previously dried at 95° C. under vacuum is combined with 125 ml of dry acetonitrile. With stirring, 14.6 g (0.053 mol) of t-butyl diphenyl chlorosilane was added. Then, 5.6 g (0.055 mol) of distilled triethylamine was added drop-wise. The mixture was allowed to react in a temperature range of 25°–30° C., then allowed to stand for three days. Anhydrous ethyl ether was added and the mixture filtered. The filtrate was concentrated in vacuum to give an oil containing a small amount of solid. The mixture was taken up in fresh anhydrous ether and again filtered. The second filtrate was dried in vacuum to yield a yellow gum or glass containing a white solid. The yellow gum was again treated with ethyl ether and a white solid was filtered off. The third filtrate was concentrated in vacuum to give a yellow glass which proved to be the desired product having an analysis as follows:

Calc'd. for $C_{38}H_{50}NO_5PSi_2$: C, 66.34; H, 7.33; N, 2.04, Found: C, 66.25; H, 7.59; N, 1.77.

EXAMPLE 2

Preparation of Glycine, N((([(1,1-Dimethylethyl)Diphenylsilyl]oxy)-Hydroxyphosphinyl)-, methyl)-, 1-Methylethyl Ester A portion of the product of Example 1 was treated with aqueous acetone at a temperature of 27° C. for 48 hours which produced a white solid. After filtering off the solid and washing with petroleum ether, it was dried in vacuum and found to have a melting point of 199°–205° C. Elemental analysis indicated that the white solid was the desired monoester having an analysis as follows:

Calc'd. for $C_{22}H_{32}NO_5PSi$: C, 58.77; H, 7.18, Found: C, 58.58; H, 7.21.

EXAMPLE 3

Preparation of Glycine, N-((([(1,1-Dimethylethyl)Dimethylsilyl]oxy)Hydroxyphosphinyl)Methyl)-, Butyl Ester To a dried and purged 500 ml flask containing 6.75 g (0.030 mol) of butyl N-phosphonomethylglycinate was added 100 ml of dry acetonitrile and 9.9 g (0.066 mol) of t-butyl dimethyl chlorosilane. While being agitated there was added to the mixture dropwise 6.7 g (0.066 mol) of triethylamine in 5 ml of acetonitrile at 30°–35° C. The reaction mixture was continually stirred over a period of two days at room temperature. The reaction mixture was then diluted with 200 ml of dry ether and stirred for one-half hour before filtering under nitrogen pressure. The filtrate was cooled resulting in the precipitation of triethylamine hydrochloride formed during the initial reaction. After filtering off the solids the filtrate was concentrated at reduced pressure to provide an oil containing a crystalline solid. The mixture was dissolved in 100 ml of petroleum ether and the solution filtered. The filtrate was concentrated to provide an oil (14.5 g). The oil was subjected to IR spectral analysis which indicated that it was the disilyl ester. This product was readily hyrolyzed to the desired product by contact with moist air in petroleum ether solution for two hours. The precipitated solid was collected and washed with petroleum ether and dried under nitrogen. The white solid had a melting point of 132° C.

Calc'd. for $C_{13}H_{30}N_1O_5PSi$: C, 45.99; H, 8.92; N, 4,13, Found: C, 45.82; H, 9.18; N, 3.95.

EXAMPLE 4

Preparation of Glycine,
N-((Bis[((1,1-Dimethylethyl)Diphenylsilyl)oxy]-Phosphinyl)-Methyl)-,
[(1,1-Dimethylethyl)Diphenylsilyl]Ester, (75%);
Silanol, (1,1-Dimethylethyl)Diphenyl-, (25%-Mixture)

A 500 ml flask equipped with a stirrer, condenser, thermometer, and addition funnel was evacuated with flaming and purged with nitrogen. To the flask was added 5.1 g (0.030 mol) of N-phosphonomethylglycine and the apparatus was again evacuated and nitrogen purged. 100 ml of dry acetonitrile and 19.35 g (0.0705 mol) of t-butyl diphenyl chlorosilane were then added and the mixture agitated. During agitation there was added 10.6 g (0.105 mol) of triethylamine over a period of about 5 minutes. The resulting mixture was agitated at 50° C. overnight. After this interval, 0.1 g of 4-dimethylaminopyridine was added as a catalyst and stirring continued at 50° C. for another 24 hours. IR analysis of the precipitate indicated the presence of N-phosphonomethylglycine and therefor an additional 9.5 g (0.0345 mol) of t-butyl diphenyl chlorosilane was added and stirring continued at 50° C. for another 24 hours.

The reaction was then cooled to room temperature and diluted with 150 ml of ether. After about 10 minutes of stirring the mixture was filtered under nitrogen. The filtrate was again filtered to remove all solids then concentrated under vacuum to provide 31.9 g of a viscous oil. The oil was redissolved in petroleum ether twice with filtering to remove solids and the residue again concentrated to yield 31 g of oil which was soluble in tetrahydrofuran. Elemental analysis of the oil indicated that it was the desired product in admixture with (1,1-dimethylethyl) diphenyl silanol.

EXAMPLE 5

Preparation of Glycine,
N-((([(1,1-Dimethylethyl)Diphenylsilyl]oxy)-Hydroxyphosphinyl)-Methyl)-, The product of Example 4 was subjected to several sequential concentrations and dilutions with wet acetonitrile and ether followed by air drying. After each dilution solids were removed. The solids obtained as a precipitate were washed with ether to provide a white powder having a melting point of 208°-210° C., which, upon elemental analysis, was found to be the desired monoester.

Calc'd. for $C_{19}H_{26}NO_5PSi$: C, 55.99; H, 6.44; N, 3.44, Found: C, 55.81; H, 6.56 N, 3,30.

Other compounds of this invention were prepared in accordance with the procedures indicated above. In Table I below are shown the reactants, reaction conditions, and analytical results for the products of the reactions.

TABLE I

| Example No. | Reactants | Reaction Temp. °C. |
|---|---|---|
| 6 | n-butyl N—phosphonomethylglycinate + t-butyl diphenyl chlorosilane | 30–35 |
| 7 | ethyl N—phosphonomethylglycinate + t-butyl diphenyl chlorosilane | 35–37 |
| 8 | 2-chloroethyl N—phosphonomethylglycinate + t-butyl diphenyl chlorosilane | room temp. |
| 9 | N—phosphonomethylglycine + t-butyl dimethyl chlorosilane | room temp. |
| 10 | 2-phenylethyl N—phosphonomethylglycinate + t-butyl dimethyl chlorosilane | room temp. |

| Example No. | Product | M.P. °C. | Analysis | |
|---|---|---|---|---|
| 6 | Glycine, N—((([(1,1-Dimethylethyl)Diphenylsilyl] Oxy)Hydroxyphosphinyl) methyl)-Butyl Ester | 133–138 | $C_{23}H_{34}NO_5PSi$ | |
| | | | Calc'd. | Found |
| | | | C, 59.58 | 59.01 |
| | | | H, 7.41 | 7.43 |
| | | | N, 3.02 | 3.05 |
| 7 | Glycine, N—((([(1,1-Dimethylethyl)Diphenylsilyl] Oxy)Hydroxyphosphinyl) Methyl)-,Ethyl Ester | 130.5–134 | $C_{21}H_{30}NO_5PSi$ | |
| | | | Calc'd. | Found |
| | | | C, 57.99 | 57.64 |
| | | | H, 6.96 | 7.03 |
| | | | N, 3.22 | 3.13 |
| 8 | Glycine, N—((([(1,1-Dimethylethyl)Diphenylsilyl] oxy)Hydroxyphosphinyl) Methyl)-,2-Chloroethyl Ester Hydrate | 137–141 | $C_{21}H_{29}ClNO_5PSi \cdot H_2O$ | |
| | | | Calc'd. | Found |
| | | | C, 51.64 | 51.90 |
| | | | H, 6.40 | 6.32 |
| | | | N, 2.87 | 2.87 |
| 9 | Glycine, N—((Bis[((1,1-Dimethylethyl)Dimethylsilyl)Oxy]Phosphinyl) Methyl),-(1,1-Dimethylethyl) Dimethylsilylester | Yellow Oil | $C_{21}H_{50}NO_5PSi_3$ | |
| | | | Calc'd. | Found |
| | | | C, 49.28 | 48.39 |
| | | | N, 2.74 | 2.63 |
| 10 | Glycine, N—((Bis[((1,1-Dimethylethyl)Dimethylsilyl) Oxy]Phosphinyl)Methyl)-,2-Phenylethyl Ester Hydrate | Orange Gum | $C_{23}H_{44}NO_5PSi_2$ | |
| | | | Calc'd. | Found |
| | | | C, 53.15 | 53.30 |
| | | | H, 8.92 | 9.14 |
| | | | N, 2.70 | 2.51 |

EXAMPLE 11

The product of Example 9 is exposed to air at room temperature for 72 hours. The product is hydrolyzed to the monosilyl ester of Example 5.

The following named compounds may also be prepared by substantial repetition of the general procedures described above in Examples 1 through 11 modified as to starting materials, reaction temperatures, times, solvents, catalysts, etc., to account for the nature of the particular reactants as will be apparent to those skilled in the art.

Glycine, N-((bis-[((1,1-dimethylethyl)diphenylsilyl)oxy]phosphinyl)-methyl)-, 2-methoxyethyl ester.

Glycine, N-((([(1,1-dimethylbutyl)dimethylsilyl]oxy)hydroxyphosphinyl)-methyl)-, methyl ester.

Glycine, N-((([(1,1-dimethylpentyl)-dimethylsilyl]oxy)hydroxyphosphinyl)-methyl)-, ethyl ester.

Glycine, N-((([(1,1-dimethylethyl)di-3,4,5-trichlorophenylsilyl]oxy)-hydroxyphosphinyl)-methyl)-, phenyl ester.

Glycine, N-((([(1,1-dimethylethyl)di-3-methoxyphenylsilyl]oxy)-hydroxyphosphinyl)-methyl)-, 2-chlorophenyl ester.

Glycine, N-((([(1,1-dimethylethyl)dimethylsilyl]oxy)-phenoxyphosphinyl)-methyl)-, phenyl ester.

Glycine, N-((([(1,1-dimethylethyl)di-3,5-dinitrophenylsilyl]oxy)hydroxyphosphinyl)-methyl)-methyl ester.

Glycine, N-((bis(((1,1-dimethylethyl)di-3-cyanophenylsilyl)oxy)hydroxyphosphinyl)-methyl)-, ethyl ester.

Glycine, N-((([(1,1-Dimethylethyl)Dimethylsilyl]oxy)-Benzyloxyphosphinyl)-methyl)-, ethyl ester.

Glycine, N-((([(1,1-dimethylethyl)diethylsilyl]oxy)-hydroxyphosphinyl)-methyl)-,4-methoxyphenyl ester.

Glycine, N-((([(1,1-dimethylethyl)di-n-butylsilyl]oxy)hydroxyphosphinyl)-methyl)-, 3-methylphenyl ester.

Glycine, N-((([(1,1-dimethylethyl)di-3-trifluoromethylphenylsilyl]oxy)hydroxyphosphinyl)-methyl)-, benzyl ester.

Glycine, N-((([(1,1-dimethylethyl)di-4-methylphenylsilyl]oxy)hydroxyphosphinyl)-methyl)-, methyl ester.

Glycine, N-((([(1,1-dimethylethyl)dimethylsilyl]oxy)-hydroxyphosphinyl)-methyl-, n-octyl ester.

Glycine, N-((([(1,1-dimethylethyl)di-n-propylsilyloxy)hydroxyphosphinyl)-methyl-, 2-phenoxy ethyl ester.

Glycine, N-((bis[((1,1-dimethylethyl)dimethylsilyl)oxy]-phosphinyl)methyl)-N-trifluoroacetyl)-, ethyl ester.

Glycine, N-(((bis[((1,1-dimethylethyl)diphenylsilyl)oxy]-phosphinyl)methyl)-N-trifluoroacetyl)-, methyl ester.

As noted above, the compounds of this invention have been found to be effective as herbicides, particularly as post-emergence herbicides.

EXAMPLE 12

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and moncotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan, except for the control pans, is removed individually to a spraying chamber and sprayed by means of an atomizer at the rates noted. In the spray solution is an amount of an emulsifying agent mixture to give a spray solution or suspension which contains about 0.4% by weight of the emulsifier. The spray solution or suspension contains a sufficient amount of the candidate chemical in order to give application rates corresponding to those set forth in the tables. The pans were returned to the greenhouse and watered as before and the injury to the plants as compared to the control is observed at approximately two and four weeks and the results recorded. In the tables, WAT means "weeks after treatment."

The post-emergent herbicidal activity index used in Tables II and III is as follows:

| Plant Response | Index |
|---|---|
| 0–24% inhibition | 0 |
| 25–49% inhibition | 1 |
| 50–74% inhibition | 2 |
| 75–99% inhibition | 3 |
| 100% inhibition | 4 |

The plant species utilized in these tests are identified by letter in accordance with the following legend:

| | |
|---|---|
| A — Canada Thistle* | K — Barnyardgrass |
| B — Cocklebur | L — Soybean |
| C — Velvetleaf | M — Sugar Beet |
| D — Morningglory | N — Wheat |
| E — Common Lambsquarters | O — Rice |
| F — Pennsylvania Smartweed | P — Grain Sorghum |
| G — Yellow Nutsedge* | Q — Wild Buckwheat |
| H — Quackgrass* | R — Hemp Sesbania |
| I — Johnsongrass* | S — Panicum Spp |
| J — Downy Brome | T — Large Crabgrass |

TABLE II

| COMPOUND | WAT | kg/h | A | B | C | D | E | F | G | H | I | J | K |
|---|---|---|---|---|---|---|---|---|---|---|---|---|---|
| Ex. 1* | 2 | 11.2 | 0 | 1 | 0 | 1 | 0 | 3 | 1 | 0 | 0 | 1 | 2 |
|  | 4 |  | 1 | 1 | 1 | 2 | 0 | 3 | 2 | 1 | 2 | 1 | 3 |
| Ex. 2* | 2 | 11.2 | 1 | 3 | 3 | 3 | 3 | 4 | 2 | 3 | 3 | 3 | 3 |
|  | 4 |  | 1 | 3 | 3 | 3 | 3 | 4 | 2 | 4 | 3 | 3 | 3 |
| * | 2 | 5.6 | 3 | 2 | 2 | 2 | 3 | 3 | 2 | 3 | 3 | 2 | 3 |
|  | 4 |  | 3 | 2 | 2 | 2 | 2 | 4 | 3 | 3 | 3 | 2 | 3 |
| Ex. 3** | 2 | 11.2 | 1 | 1 | 1 | 1 | 3 | 2 | 1 | 3 | 1 | 0 | 2 |
|  | 4 |  | 2 | 2 | 2 | 2 | 4 | 3 | 2 | 3 | 2 | 1 | 3 |
| ** | 2 | 5.6 | 1 | 1 | 0 | 1 | 3 | 1 | 1 | 0 | 0 | 0 | 2 |
|  | 4 |  | 1 | 1 | 1 | 1 | 4 | 1 | 2 | 1 | 1 | 1 | 2 |
| Ex. 4** | 2 | 11.2 | 2 | 2 | 1 | 2 | 2 | 2 | 0 | 1 | 0 | 0 | 1 |
|  | 4 |  | 2 | 2 | 1 | 2 | 3 | 2 | 2 | 2 | 1 | 0 | 1 |
| ** | 2 | 5.6 | 0 | 1 | 0 | 1 | 0 | 1 | 0 | 0 | 0 | 0 | 1 |
|  | 4 |  | 0 | 1 | 0 | 1 | 0 | 0 | 1 | 0 | 0 | 0 | 1 |

TABLE II-continued

| COMPOUND | WAT | kg/h | A | B | C | D | E | F | G | H | I | J | K |
|---|---|---|---|---|---|---|---|---|---|---|---|---|---|
| Ex. 5 | 2 | 11.2 | 1 | 2 | 1 | 1 | 1 | 2 | 1 | 0 | 1 | 0 | 1 |
|  | 4 |  | 1 | 2 | 0 | 1 | 2 | 2 | 2 | 1 | 2 | 0 | 2 |
|  | 2 | 5.6 | 1 | 2 | 0 | 1 | 1 | 0 | 0 | 0 | 0 | 0 | 0 |
|  | 4 |  | 1 | 1 | 0 | 1 | 0 | 0 | 1 | 0 | 1 | 0 | 0 |
| ** | 2 | 11.2 | 0 | 1 | 0 | 1 | 0 | 0 | 0 | 0 | 0 | 0 | 1 |
|  |  |  | 1 | 1 | 0 | 1 | 0 | 0 | 0 | 0 | 0 | 0 | 0 |
| ** |  | 5.6 | 0 | 1 | 0 | 1 | 0 | 0 | 0 | 0 | 0 | 0 | 0 |
| Ex. 6 | 2 | 11.2 | 3 | 2 | 2 | 2 | 3 | 2 | 1 | 1 | 1 | 0 | 2 |
|  | 4 |  | 4 | 2 | 1 | 2 | 4 | 2 | 2 | 4 | 0 | 1 | 3 |
|  | 2 | 5.6 | 0 | 1 | 0 | 2 | 2 | 0 | 0 | 0 | 0 | 0 | 1 |
|  |  |  | 1 | 1 | 0 | 2 | 2 | 0 | 1 | 0 | 2 | 0 | 2 |
| ** | 2 | 11.2 | 0 | 1 | 0 | 2 | 3 | 0 | 0 | 0 | 0 | 0 | 1 |
|  | 4 |  | 1 | 2 | 1 | 2 | 4 | 0 | 1 | 0 | 1 | 0 | 1 |
| ** | 2 | 5.6 | 0 | 1 | 0 | 1 | 1 | 0 | 0 | 0 | 0 | 0 | 1 |
|  | 4 | 5.6 | 0 | 1 | 0 | 2 | 3 | 0 | 1 | 1 | 1 | 0 | 2 |
| Ex. 7 | 2 | 11.2 | — | 2 | 3 | 2 | 4 | 2 | 2 | 2 | 4 | 2 | 3 |
|  | 4 |  | — | 4 | 3 | 2 | 4 | 2 | 3 | 3 | 4 | 3 | 4 |
|  | 2 | 5.6 | — | 3 | 2 | 2 | 3 | 2 | 1 | 1 | 3 | 2 | 3 |
| Ex. 7 | 4 |  | — | 4 | 3 | 2 | 3 | 4 | 2 | 4 | 4 | 3 | 3 |
| ** | 2 | 11.2 | 1 | 1 | 1 | 1 | 4 | 1 | 1 | 1 | 0 | 1 | 2 |
|  | 4 |  | 3 | 3 | 1 | 2 | 4 | 4 | 2 | 2 | 1 | 1 | 3 |
| ** | 2 | 5.6 | 1 | 2 | 1 | 2 | 3 | 1 | 1 | 1 | 0 | 1 | 1 |
|  | 4 |  | 3 | 3 | 2 | 2 | 3 | 1 | 2 | 2 | 2 | 1 | 2 |
| Ex. 8 | 2 | 11.2 | 2 | 3 | 3 | 2 | 1 | 2 | 2 | 2 | 1 | 2 | 2 |
|  | 4 |  | 2 | 3 | 3 | 2 | 1 | 4 | 3 | 3 | 2 | 3 | 3 |
|  | 2 | 5.6 | 2 | 2 | 1 | 2 | 2 | 3 | 2 | 3 | 0 | 1 | 3 |
|  | 4 |  | 4 | 3 | 1 | 2 | 2 | 4 | 2 | 4 | 2 | 1 | 4 |
| Ex. 9* | 2 | 11.2 | 1 | 2 | 2 | 2 | 0 | 1 | 1 | 0 | 1 | 1 | 1 |
|  | 4 |  | 1 | 2 | 2 | 2 | 2 | 1 | 2 | 0 | 1 | 1 | 2 |
| * | 2 | 5.6 | 1 | 1 | 1 | 2 | 0 | 1 | 1 | 0 | 1 | 0 | 1 |
|  | 4 |  | 2 | 2 | 1 | 2 | 1 | 1 | 2 | 0 | 1 | 1 | 1 |
| Ex. 10* | 2 | 11.2 | 2 | 2 | 2 | 2 | 3 | 3 | 2 | 1 | 1 | 1 | 2 |
|  | 4 |  | 2 | 2 | 2 | 2 | 3 | 3 | 2 | 1 | 1 | 1 | 3 |
| * | 2 | 5.6 | 0 | 1 | 0 | 1 | 2 | 1 | 1 | 0 | 0 | 0 | 1 |
|  | 4 |  | 0 | 0 | 0 | 0 | 3 | 1 | 2 | 0 | 0 | 0 | 2 |

*Formulated immediately prior to treatment.
**Formulated in anhydrous tetrahydrofuran.

TABLE III

| COMPOUND | WAT | kg/h | L | M | N | O | P | B | Q | D | R | E | F | C | J | S | K | T |
|---|---|---|---|---|---|---|---|---|---|---|---|---|---|---|---|---|---|---|
| Ex. 1 | 2 | 5.6 | 1 | 3 | 3 | 3 | 3 | 2 | 3 | 2 | 2 | 3 | 3 | 2 | 3 | 3 | 4 | 4 |
|  | 2 | 1.1 | 0 | 1 | 0 | 0 | 0 | 0 | 0 | 0 | 0 | 0 | 0 | 0 | 0 | 0 | 1 | 2 |
| Ex. 2 | 2 | 5.6 | 2 | 2 | 3 | 3 | 3 | 3 | 3 | 3 | 3 | 3 | 3 | 3 | 3 | 3 | 3 | 3 |
|  | 2 | 1.1 | 0 | 0 | 1 | 0 | 1 | 0 | 0 | 0 | 3 | 3 | 0 | 0 | 0 | 0 | 1 | 2 |
| Ex. 3** | 2 | 5.6 | 2 | 2 | 3 | 1 | 1 | 2 | 3 | 2 | 4 | 4 | 3 | 3 | 1 | 3 | 2 | 4 |
|  | 4 |  | 2 | 3 | 3 | 2 | 2 | 3 | 4 | 2 | 4 | 4 | 3 | 4 | 1 | 3 | 3 | 4 |
|  | 2 | 1.1 | 2 | 1 | 1 | 0 | 1 | 2 | 2 | 2 | 1 | 3 | 2 | 2 | 1 | 1 | 2 | 3 |
|  | 4 |  | 1 | 1 | 1 | 1 | 1 | 1 | 2 | 2 | 1 | 3 | 2 | 2 | 1 | 2 | 2 | 4 |
|  | 2 | .28 | 1 | 0 | 2 | 1 | 0 | 2 | 1 | 1 | 1 | 3 | 2 | 1 | 1 | 1 | 1 | 3 |
|  | 4 |  | 0 | 0 | 1 | 0 | 0 | 1 | 0 | 1 | 0 | 4 | 2 | 2 | 0 | 1 | 1 | 4 |
| Ex. 5** | 2 | 5.6 | 1 | 0 | 0 | 0 | 0 | 0 | 1 | 1 | 0 | 0 | 1 | 0 | 0 | 0 | 0 | 1 |
|  | 4 |  | 0 | 0 | 0 | 0 | 0 | 0 | 0 | 0 | 1 | 1 | 0 | 0 | 0 | 0 | 0 | 1 |
| ** | 2 | 1.1 | 1 | 0 | 0 | 0 | 3 | 1 | 0 | 0 | 0 | 0 | 0 | 0 | 0 | 0 | 0 | 0 |
| ** | 2 | .28 | 1 | 0 | 0 | 0 | 0 | 1 | 0 | 0 | 0 | 0 | 0 | 0 | 0 | 0 | 0 | 0 |
| Ex. 6 | 2 | 5.6 | 1 | 2 | 3 | 2 | 3 | 3 | 2 | 2 | 2 | 3 | 3 | 2 | 1 | 4 | 3 | 4 |
|  | 4 |  | 1 | 3 | 3 | 3 | 3 | 3 | 3 | 3 | 2 | 3 | 3 | 2 | 3 | 4 | 3 | 4 |
|  | 2 | 1.1 | 1 | 1 | 1 | 1 | 1 | 2 | 2 | 2 | 1 | 3 | 2 | 1 | 1 | 3 | 2 | 4 |
|  | 4 |  | 1 | 1 | 1 | 1 | 1 | 2 | 1 | 2 | 1 | 3 | 3 | 1 | 1 | 3 | 2 | 4 |
|  | 2 | .28 | 0 | 0 | 1 | 0 | 1 | 0 | 1 | 1 | — | 3 | 3 | 0 | 1 | 2 | 2 | 4 |
| ** | 2 | 5.6 | 2 | 1 | 2 | 1 | 1 | 2 | 2 | 2 | 4 | 3 | — | 2 | 1 | 2 | 2 | 4 |
|  | 4 |  | 2 | 1 | 2 | 2 | 2 | 2 | 2 | 2 | 4 | 4 | — | 2 | 2 | 3 | 2 | 4 |
| ** | 2 | 1.1 | 1 | 1 | 2 | 0 | 1 | 1 | 2 | 2 | 1 | 3 | 3 | 1 | 1 | 2 | 2 | 4 |
|  | 4 |  | 1 | 1 | 1 | 0 | 1 | 1 | 2 | 2 | 0 | 4 | 4 | 1 | 1 | 2 | 2 | 4 |
| ** | 2 | .28 | 1 | 0 | 0 | 0 | 0 | 1 | 1 | 1 | 0 | 1 | 1 | 0 | 0 | 0 | 0 | 1 |
|  |  |  | 1 | 0 | 0 | 0 | 0 | 1 | 1 | 1 | 0 | 1 | 1 | 0 | 0 | 0 | 0 | 0 |
| Ex. 7 | 2 | 5.6 | 2 | 1 | 2 | 2 | 3 | 2 | 2 | 2 | 1 | 3 | 2 | 2 | 2 | 3 | 3 | — |
|  | 4 |  | 1 | 2 | 3 | 3 | 3 | 3 | 3 | 3 | 2 | 3 | 3 | 2 | 2 | 4 | 3 | — |
|  | 2 | 1.1 | 2 | 1 | 2 | 2 | 3 | 2 | 2 | 2 | 3 | 4 | 3 | 1 | 2 | 4 | 3 | 4 |
|  | 4 |  | 1 | 1 | 3 | 3 | 3 | 3 | 2 | 2 | 4 | 4 | 3 | 1 | 2 | 4 | 3 | 4 |
|  | 2 | .28 | 0 | 1 | 2 | 2 | 2 | 1 | 2 | 2 | 1 | 3 | 3 | 1 | 1 | 3 | 2 | — |
|  | 4 |  | 0 | 1 | 1 | 1 | 1 | 2 | 1 | 2 | 1 | 3 | 3 | 1 | 0 | 3 | 2 | — |
| ** | 2 | 5.6 | 2 | 3 | 3 | 3 | 2 | 3 | 3 | 2 | 1 | 4 | 4 | 2 | 2 | 4 | 3 | 3 |
|  | 4 |  | 2 | 4 | 3 | 3 | 3 | 3 | 3 | 3 | 1 | 4 | 4 | 3 | 3 | 4 | 3 | 3 |
| ** | 2 | 1.1 | 1 | 1 | 2 | 1 | 1 | 2 | 2 | 2 | 2 | 4 | 4 | 2 | 1 | 2 | 2 | 3 |
|  | 4 |  | 1 | 1 | 2 | 1 | 2 | 2 | 2 | 2 | 2 | 4 | 4 | 2 | 1 | 2 | 2 | 3 |
| ** | 2 | .28 | 1 | 1 | 1 | 1 | 1 | 2 | 1 | 1 | 0 | 2 | 2 | 1 | 0 | 1 | 1 | 2 |
|  | 4 |  | 1 | 1 | 1 | 0 | 0 | 2 | 1 | 1 | 0 | 3 | 2 | 1 | 0 | 1 | 1 | 2 |
| Ex. 8 | 2 | 1.1 | 0 | 0 | 0 | 0 | 0 | 0 | 0 | 0 | 1 | 3 | — | 0 | 0 | 1 | 1 | 2 |
| Ex. 10 | 2 | 5.6 | 0 | 3 | 0 | 0 | 0 | 2 | 0 | 0 | 0 | 3 | 2 | 2 | 1 | 3 | 2 | 3 |

TABLE III-continued

| COMPOUND | WAT | kg/h | L | M | N | O | P | B | Q | D | R | E | F | C | J | S | K | T |
|---|---|---|---|---|---|---|---|---|---|---|---|---|---|---|---|---|---|---|
| | 2 | 1.1 | 0 | 2 | 0 | 0 | 0 | 0 | 0 | 2 | 0 | 2 | 2 | 1 | 0 | 3 | 0 | 3 |
| | 2 | 1.1 | 0 | 0 | 0 | 0 | 0 | 0 | 0 | 0 | 2 | — | 0 | 0 | 0 | 1 | 2 | |

**Formulated in anhydrous tetrahydrofuran.

From the test results presented in Tables II and III, it can be seen that the postemergent herbicidal activity of the compounds of this invention is, for the most part, general in nature.

Typically, herbicidal compounds of this invention are provided in the form of concentrates which require dilution prior to application to plants. The usual means for diluting the herbicide is the preparation of herbicidal compositions wherein the compound possessing herbicidal activity is mixed with other materials. Such other materials may be in either liquid or solid form and comprise adjuvants, inert materials, etc.

The herbicidal composition containing herbicidal compounds of this invention are prepared in the usual manner by combining them with other materials which are well known in the herbicide art. The following is a description of herbicidal compositions employing the herbicidal compounds of this invention together with known materials and formulations typically utilized in the herbicide art.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant, and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers, and conditioning agents to provide compositions in the form of finely-divided solid, a liquid of organic origin, water, a wetting agent, a dispersing agent, an emulsifying agent, or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic, and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl napthalene sulfonates, sodium naphthalene sulfonate, polymethylene bisnaphthalenesulfonate and sodium N-methyl-N-(long chain acid) taurates.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific N-phosphonomethylglycine derivatives employed. In foliar treatment for the control of vegetative growth, the active ingredients are applied in amounts from about 0.112 to about 56.0 or more kilograms per hectare. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15-17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compounds or compositions employed will determine to a large extent the particular application method selected therefor.

The aforementioned and other possible methods for applying liquid compositions to plants are discussed in detail in "Rope Wick Applicator—Tool with a Future," Dale, James E., pp. 3-4, "The Recirculating Sprayer and Roundup ® Herbicide," Derting, Claude W., pp. 5-7, and "C.D.A. Herbicide Application," McGarvey, Frank X., Weeds Today, Volume 11, Number 2, pp. 8-9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes, and modifications may be resorted to without departing from the spirit and scope thereof and it is understood that such equivalent embodiments are intended to be included herein.

I claim:

1. A compound represented by the structure

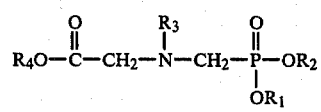

wherein $R_1$ and $R_2$ are independently selected from hydrogen, aryl, benzyl, substituted aryl and substituted benzyl groups, and X wherein X is

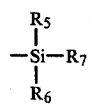

wherein $R_5$ and $R_6$ are independently selected from alkyl groups having from 1 to 4 carbon atoms, phenyl and phenyl substituted with from 1 to 3 substituents selected from halogen, lower alkyl lower alkoxy, trifluoromethyl, nitro and cyano and $R_7$ is a tertiary alkyl group having from 4 to 7 carbon atoms, $R_3$ is hydrogen or a herbicidally non-interfering group, and $R_4$ is selected from hydrogen, X, alkyl groups having from 1 to 8 carbon atoms, naphthyl, phenyl and phenyl substituted with from 1 to 3 substituents selected from halogen, lower alkyl lower alkoxy, nitro, trifluoromethyl, and cyano provided that at least one of $R_1$, $R_2$, and $R_4$ is X.

2. A compound of claim 1 wherein $R_3$ is hydrogen.
3. A compound of claim 1 wherein $R_4$ is alkyl.
4. A compound of claim 1 wherein $R_1$, $R_2$, and $R_4$ are X.
5. A compound of claim 4 wherein $R_3$ is hydrogen.
6. A compound of claim 4 wherein $R_7$ is 1,1-dimethylethyl.
7. A compound of claim 1 wherein $R_1$ is X and $R_2$ and $R_3$ are hydrogen.
8. A compound of claim 1 wherein $R_1$ and $R_2$ are X and $R_3$ and $R_4$ are hydrogen.
9. A compound of claim 1 wherein $R_5$ and $R_6$ are alkyl and $R_7$ is 1,1-dimethylethyl.
10. A compound of claim 1 wherein $R_5$ and $R_6$ are phenyl or phenyl substituted with from 1 to 3 substituents selected from halogen, lower alkyl lower alkoxy, nitro and cyano.
11. A compound of claim 9 wherein $R_5$ and $R_6$ are methyl.
12. A compound of claim 1 wherein $R_1$ and $R_2$ are X, $R_3$ is hydrogen, and $R_4$ is lower alkoxy lower alkyl.
13. A compound of claim 7 wherein $R_4$ is hydrogen, $R_5$ and $R_6$ are phenyl, and $R_7$ is 1,1-dimethylethyl.
14. A compound of claim 7 wherein $R_4$ is alkyl.
15. A compound of claim 14 wherein $R_4$ is n-butyl, $R_5$ and $R_6$ are phenyl, and $R_7$ is 1,1-dimethylethyl.
16. A compound of claim 7 wherein $R_4$ is n-butyl, $R_5$ and $R_6$ are methyl, and $R_7$ is 1,1-dimethylethyl.
17. A compound of claim 7 wherein $R_4$ is haloalkyl.
18. A compound of claim 17 wherein $R_4$ is 2-chloroethyl, $R_5$ and $R_6$ are phenyl, and $R_7$ is 1,1-dimethylethyl.
19. A compound of claim 4 wherein $R_3$ is hydrogen, $R_5$ and $R_6$ are phenyl, and $R_7$ is 1,1-dimethylethyl.
20. A compound of claim 1 wherein $R_1$ and $R_2$ are X.
21. A compound of claim 20 wherein $R_3$ is hydrogen and $R_4$ is alkyl.
22. A compound of claim 21 wherein $R_4$ is methylethyl, $R_5$ and $R_6$ are phenyl, and $R_7$ is 1,1-dimethylethyl.
23. A herbicidal composition which comprises an inert adjuvant and a herbicidally affective amount of a compound of the formula

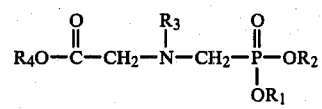

wherein $R_1$ and $R_2$ are independently selected from hydrogen, aryl, benzyl substituted aryl and substituted benzyl, and X wherein X is

wherein $R_5$ and $R_6$ are independently selected from alkyl groups having from 1 to 4 carbon atoms, phenyl and phenyl substituted with from 1 to 3 substituents selected from halogen, lower alkyl lower alkoxy, —$CF_3$, nitro and cyano and $R_7$ is a tertiary alkyl group having from 4 to 7 carbon atoms, $R_3$ is hydrogen or a herbicidally non-interfering group, and $R_4$ is selected from hydrogen, X, alkyl groups having from 1 to 8 carbon atoms, naphthyl, phenyl and phenyl substituted with from 1 to 3 substituents selected from halogen, lower alkyl lower alkoxy, nitro, trifluoromethyl, and cyano provided that at least one of $R_1$, $R_2$, and $R_4$ is X.

24. A herbicidal composition of claim 23 wherein $R_3$ is hydrogen.

25. A herbicidal composition of claim 23 wherein $R_4$ is alkyl.

26. A herbicidal composition of claim 23 wherein $R_1$, $R_2$, $R_4$ are X.

27. A herbicidal composition of claim 26 wherein $R_3$ is hydrogen.

28. A herbicidal composition of claim 26 wherein $R_7$ is 1,1-dimethylethyl.

29. A herbicidal composition of claim 23 wherein $R_1$ is X and $R_2$ and $R_3$ are hydrogen.

30. A herbicidal composition of claim 23 wherein $R_1$ and $R_2$ are X and $R_3$ and $R_4$ are hydrogen.

31. A herbicidal composition of claim 23 wherein $R_5$ and $R_6$ are alkyl and $R_7$ is 1,1-dimethylethyl.

32. A herbicidal composition of claim 23 wherein $R_5$ and $R_6$ are phenyl or phenyl substituted with from 1 to 3 substituents selected from halogen, lower alkyl- loweralkoxy, nitro and cyano.

33. A herbicidal composition of claim 31 wherein $R_5$ and $R_6$ are methyl.

34. A herbicidal composition of claim 23 wherein $R_1$ and $R_2$ are X, $R_3$ is hydrogen, and $R_4$ is lower alkoxy, lower alkyl.

35. A herbicidal composition of claim 29 wherein $R_4$ is hydrogen, $R_5$ and $R_6$ are phenyl, and $R_7$ is 1,1-dimethylethyl.

36. A herbicidal composition of claim 29 wherein $R_4$ is alkyl.

37. A herbicidal composition of claim 36 wherein $R_4$ is n-butyl, $R_5$ and $R_6$ are phenyl, and $R_7$ is 1,1-dimethylethyl.

38. A herbicidal composition of claim 29 wherein $R_4$ is n-butyl, $R_5$ and $R_6$ are methyl, and $R_7$ is 1,1-dimethylethyl.

39. A herbicidal composition of claim 29 wherein $R_4$ is haloalkyl.

40. A herbicidal composition of claim 39 wherein $R_4$ is 2-chloroethyl, $R_5$ and $R_6$ are phenyl, and $R_7$ is 1,1-dimethylethyl.

41. A herbicidal composition of claim 26 wherein $R_3$ is hydrogen, $R_5$ and $R_6$ are phenyl, and $R_7$ is 1,1-dimethylethyl.

42. A herbicidal composition of claim 23 wherein $R_1$ and $R_2$ are X.

43. A herbicidal composition of claim 42 wherein $R_3$ is hydrogen and $R_4$ is alkyl.

44. A herbicidal composition of claim 43 wherein $R_4$ is methylethyl, $R_5$ and $R_6$ are phenyl, and $R_7$ is 1,1-dimethylethyl.

45. A method which comprises contacting a plant with a herbicidally effective amount of a compound of claim 1.

46. A method of claim 45 wherein $R_3$ is hydrogen.

47. A method of claim 45 wherein $R_4$ is alkyl.

48. A method of claim 45 wherein $R_1$, $R_2$, and $R_4$ are X.

49. A method of claim 48 wherein $R_3$ is hydrogen.

50. A method of claim 48 wherein $R_7$ is 1,1-dimethylethyl.

51. A method of claim 45 wherein $R_1$ is X and $R_2$ and $R_3$ are hydrogen.

52. A method of claim 45 wherein $R_1$ and $R_2$ are X and $R_3$ and $R_4$ are hydrogen.

53. A method of claim 45 wherein $R_5$ and $R_6$ are alkyl and $R_7$ is 1,1-dimethylethyl.

54. A method of claim 45 wherein $R_5$ and $R_6$ are phenyl or phenyl substituted with from 1 to 3 substituents selected from halogen, lower alkylloweralkoxy, nitro and cyano.

55. A method of claim 53 wherein $R_5$ and $R_6$ are methyl.

56. A method of claim 45 wherein $R_1$ and $R_2$ are X, $R_3$ is hydrogen, and $R_4$ is lower alkoxy, lower alkyl.

57. A method of claim 51 wherein $R_4$ is hydrogen, $R_5$ and $R_6$ are phenyl, and $R_7$ is 1,1-dimethylethyl.

58. A method of claim 51 wherein $R_4$ is alkyl.

59. A method of claim 58 wherein $R_4$ is n-butyl, $R_5$ and $R_6$ are phenyl, and $R_7$ is 1,1-dimethylethyl.

60. A method of claim 51 wherein $R_4$ is n-butyl, $R_5$ and $R_6$ are methyl, and $R_7$ is 1,1-dimethylethyl.

61. A method of claim 51 wherein $R_4$ is haloalkyl.

62. A method of claim 61 wherein $R_4$ is 2-chloroethyl, $R_5$ and $R_6$ are phenyl, and $R_7$ is 1,1-dimethylethyl.

63. A method of claim 48 wherein $R_3$ is hydrogen, $R_5$ and $R_6$ are phenyl, and $R_7$ is 1,1-dimethylethyl.

64. A method of claim 45 wherein $R_1$ and $R_2$ are X.

65. A method of claim 64 wherein $R_3$ is hydrogen and $R_4$ is alkyl.

66. A method of claim 65 wherein $R_4$ is methylethyl, $R_5$ and $R_6$ are phenyl, and $R_7$ is 1,1-dimethylethyl.

67. A compound of claim 1 wherein $R_5$ and $R_6$ are trifluoromethyl.

* * * * *

UNITED STATES PATENT AND TRADEMARK OFFICE
CERTIFICATE OF CORRECTION

PATENT NO. : 4,471,131
DATED : September 11, 1984
INVENTOR(S) : John E. Franz

It is certified that error appears in the above-identified patent and that said Letters Patent is hereby corrected as shown below:

Column 4, line 68: "4,13," should be --4.13,--

Column 6, Table I, Example 9:

between "C, 49.28   48.39
            N, 2.74    2.63"

insert --H, 9.85   10.01--

Column 8, after line 53: insert --*--Established from vegetative propagules.--

Column 15, Claim 26, line 9: after "$R_2$," insert --and--

Signed and Sealed this

*Nineteenth* Day of *February 1985*

[SEAL]

*Attest:*

DONALD J. QUIGG

*Attesting Officer*     *Acting Commissioner of Patents and Trademarks*